(12) United States Patent
Yao et al.

(10) Patent No.: US 9,884,047 B1
(45) Date of Patent: Feb. 6, 2018

(54) METHOD OF TREATING LUNG CANCER

(71) Applicant: Macau University of Science and Technology, Macau (CN)

(72) Inventors: Xiao Jun Yao, Macau (CN); Lai Han Elaine Leung, Macau (CN); Liang Liu, Macau (CN); Xing Xing Fan, Macau (CN); Chun Xie, Macau (CN)

(73) Assignee: Macau University of Science and Technology, Macau (CN)

( * ) Notice: Subject to any disclaimer, the term of this patent is extended or adjusted under 35 U.S.C. 154(b) by 0 days.

(21) Appl. No.: 15/632,407

(22) Filed: Jun. 26, 2017

(51) Int. Cl.
| | |
|---|---|
| *A61K 31/428* | (2006.01) |
| *G01N 33/574* | (2006.01) |
| *C07D 277/72* | (2006.01) |
| *C07K 14/47* | (2006.01) |
| *C12Q 1/68* | (2006.01) |
| *G01N 33/68* | (2006.01) |
| *A61K 38/00* | (2006.01) |

(52) U.S. Cl.
CPC .......... *A61K 31/428* (2013.01); *C07D 277/72* (2013.01); *C07K 14/47* (2013.01); *C12Q 1/6886* (2013.01); *G01N 33/57423* (2013.01); *G01N 33/57484* (2013.01); *A61K 38/00* (2013.01); *C07K 2319/00* (2013.01); *C12Q 2600/112* (2013.01); *G01N 33/574* (2013.01); *G01N 33/68* (2013.01)

(58) Field of Classification Search
None
See application file for complete search history.

(56) References Cited

U.S. PATENT DOCUMENTS

2008/0227640 A1* 9/2008 Bastiaans .............. A01N 43/38
504/284

OTHER PUBLICATIONS

Azizian, J., et al., Med. Chem. Res., 21:3730 (Year: 2012).*
Detterbeck, F.C., et al. (2013). Diagnosis and Management of Lung Cancer. Chest, 143(5) (Suppl), 7S-37S.
Gremer, L.,et al. (2010). Germline KRAS Mutations Cause Aberrant Biochemical and Physical Properties Leading to Developmental Disorders. Human Mutation, 32(1), 33-43.
Schubbert, S., Shannon K., Bollag, G. (2007). Hyperactive Ras in developmental disorders and cancer. Nature Cancer, 7, 295-308.
Baines, A.T., Xu, D., Der, C. J. (2011). Inhibition of Ras for cancer treatment: the search continues. Future Med. Chem, 3(14), 1787-1808.
White, Y., et al. (2016). KRAS insertion mutations are oncogenic and exhibit distinct functional properties, Nat Commun, 7, 1-8.
Wakelee, H., et al. (2007). Lung Cancer Incidence in never Smokers. J Clin Oncol, 25, 472-478.
Molina, Jr., et al. (2008). Non-Small Cell Lung Cancer: Epidemiology, Risk Factors, Treatment, and Survivorship. Mayo Clin Proc., 83(5), 584-594.
Chen, Z., et al. (2014). Non-small-cell lung cancers: a heterogeneous set of diseases. Nature Cancer, 14, 535-546.
Cox, A.D., Der, C.J. (2010). Ras history: the saga continues. Small GTPases, 1(1), 2-27.
Castellano, E, Downward, J. (2011). RAS interaction with PI3K: More Than Just Another Effector Pathway. Genes & Cancer, 2(3), 261-274.
Shaw, R.J., Cantley, L.C. (2006). Ras, P1(3)K and mTOR signalling controls tumour cell growth. Nature, 441, 424-430.
Downward, J. (2003). Targeting Ras signalling pathways in cancer therapy. Nature Cancer, 3, 11-22.
Takashima, A, Faller, D.V. (2013). Targeting the RAS oncogene. Expert Opin. Ther. Targets, 17(5), 507-531.
Westcott, P.M.K. To, M.D. (2013). The genetics and biology of KRAS in lung cancer. Chin J Cancer, 32(2), 64-70.

* cited by examiner

*Primary Examiner* — Michael Barker
(74) *Attorney, Agent, or Firm* — Eagle IP Limited; Jacqueline C. Lui (57) ABSTRACT

One example embodiment relates to a method of treating non-small cell lung cancer by administering a compound of formula (I) to a patient. Another example embodiment relates to a method of inhibiting progress of tumor growth in a patient with cancer, wherein tumor cells of the cancer have a mutant V-Ki-ras2 Kirsten rat sarcoma viral oncogene homolog (KRAS) gene, and the method includes administering to the patient the compound with the following formula I:

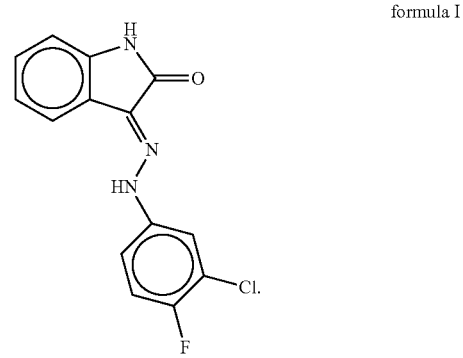

formula I

20 Claims, 11 Drawing Sheets
(5 of 11 Drawing Sheet(s) Filed in Color)

| Cell line | Mutation | IC$_{50}$ Value (μM) | | |
|---|---|---|---|---|
| | | 24h | 48h | 72h |
| A549 | KRAS(G12S) | 30.14±4.63 | 14.51±3.05 | 8.28±2.64 |
| H2122 | KRAS(G12C) | 22.25±8.31 | 14.07±2.81 | 7.19±1.60 |
| H358 | KRAS(G12C) | 20.71±5.77 | 12.86±1.60 | 8.18±1.29 |
| CCD19-Lu | N/A | >200 | >200 | >200 |

METHOD OF TREATING LUNG CANCER

FIELD OF THE INVENTION

The present invention relates to a method of treating cancer. In particular, the present invention relates to a method of treating non-small cell lung cancer (NSCLC).

BACKGROUND

Lung cancer is one of the most lethal cancers worldwide. There are two main types of lung cancer, namely, non-small lung cancer (NSCLC) and small cell lung cancer. NSCLC accounts for about 85% of all lung cancers.

In view of the demand for effectively treating lung cancer in a patient, particularly NSCLC, improvements in methods and compositions that treat lung cancer are desired.

SUMMARY OF THE INVENTION

One example embodiment is a method of treating non-small cell lung cancer (NSCLC) in a patient. The method includes administering to the patient a therapeutically effective amount of a compound of formula I to treat the NSCLC as follows:

Formula I (compound K017-0105)

Another example embodiment is a method of inhibiting progress of tumor growth in a patient with cancer of which tumor cells have or express a mutant V-Ki-ras2 Kirsten rat sarcoma viral oncogene homolog (KRAS). The method includes administering the compound of formula I to the patient to treat the cancer.

Other example embodiments are discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Example embodiments relate to methods to treat cancer by administering, to a patient, a therapeutically effective amount of a compound with the following formula I:

Formula I (compound K017-0105)

Example embodiments relate to methods to treat lung cancer, particularly non-small cell lung cancer (NSCLC) by administering the compound of formula I to a patient.

An example embodiment relates to a method of treating lung adenocarcinoma by administering the compound of formula I (i.e. compound K017-0105) to a patient to treat the lung adenocarcinoma. Tumor cells of the lung adenocarcinoma have a mutant V-Ki-ras2 Kirsten rat sarcoma viral oncogene homolog (KRAS) gene that encodes a mutant KRAS.

An example embodiment relates to a method of inhibiting progress of tumor growth in a patient with cancer, and the method includes diagnosing the patient with the cancer when a KRAS mutation is detected in the cancer cells. The method also includes administering a therapeutically effective amount of the compound of formula I to the patient with the cancer to inhibit the progress of tumor growth. Tumor cells of the cancer include, express or have mutant KRAS.

In an example embodiment, tumor cells or cancer cells express, have or include a mutant KRAS. In a further example embodiment, the mutant KRAS includes an amino acid substitution from a glycine (G) to a cysteine (C) at codon 12 ($KRAS^{G12C}$ mutation). In yet a further example embodiment, the mutant KRAS includes an amino acid substitution from a glycine (G) to a serine (S) at codon 12 ($KRAS^{G12S}$ mutation).

In an example embodiment, the tumor cells of the NSCLC have a mutant KRAS gene. In a further example embodiment, the tumor cells of the NSCLC have a mutant KRAS gene that encodes a mutant KRAS, and the mutant KRAS results in an increased level of guanosine-5'-triphosphate (GTP)-bound KRAS. In a particular example embodiment, the compound of formula I inhibits the level of GTP-bound KRAS to treat the NSCLC.

In an example embodiment, the tumor cells of the NSCLC have a mutant KRAS gene that encodes a mutant KRAS. The mutant KRAS activates phosphorylation of proto-oncogene c-RAF (CRAF), extracellular signal-regulated kinases (ERK) and Akt. In an example embodiment, the compound of formula I inhibits the phosphorylation of CRAF, ERK and Akt to treat the NSCLC. In a further example embodiment, the tumor cells of the NSCLC have a mutant KRAS gene that encodes a mutant KRAS and the mutant KRAS results in an increased level of GTP-bound KRAS and activates phosphorylation of CRAF, ERK and Akt. In an example embodiment, the compound of formula I inhibits the level of GTP-bound KRAS in tumor cells and inhibits the phosphorylation of CRAF, ERK and Akt to treat the NSCLC.

Mutant KRAS have impaired GTPase activity resulting in KRAS being locked in an active GTP-bound state and constitutive activation of KRAS signaling pathways. Cellular pathways including the Raf/mitogen-activated protein kinase kinase (MEK)/extracellular signal-regulated kinases (ERK) pathway and the phosphatidylinositol 3-kinase/Akt pathway are activated by deregulation of KRAS signaling in mutant KRAS.

Example embodiments provide a compound of formula I that can impair the KRAS signaling pathway that is used to treat cancer, particularly lung cancer or NSCLC. The compound exhibits significant inhibitory effect on the level of GTP-bound KRAS and deregulates phosphorylation of CRAF, ERK and Akt in A549, H2122 and H358 NSCLC cell lines and significantly induces apoptosis in A549, H2122 and H358 NSCLC cell lines.

Example 1

Material and Methods
1. Cell Culture
H2122, A549 and H358 non-small cell lung cancer (NSCLC) cells were purchased from ATCC and cultivated with Roswell Park Memorial Institute (RPMI) 1640 medium supplemented with 10% fetal bovine serum (Gibco, Big Cabin, Oklahoma, ME, USA), 100 units/mL penicillin and 100 μg/mL streptomycin (Gibco, Big Cabin, Oklahoma, ME, USA). All the cells were cultivated at 37° C. in a humidified atmosphere of 5% $CO_2$.

1.1 MTT Cytotoxicity Assay
Cells were seeded in a 96-well microplate with 3000, 4000 or 5000 cells/well confluence and cultured overnight for cell adhesion. Different concentrations of compound K017-0105 were added to the microplates, and the microplates were incubated for 24, 48 or 72 hours (h). Each concentration of compound K017-0105 was repeated in triplicate. 10 μL 3-(4,5-Dimethylthiazol-2-yl)-2,5-Diphenyltetrazolium Bromide (MTT) (5 mg/mL) solution was added to every well. After incubating for 4 h, 100 μL dimethyl sulfoxide (DMSO) was added to each well. After shaking for 15 minutes, the absorbance of the microplate was measured at 570 nm (absorbance) and 650 nm (reference) by a microplate reader (Tecan, Morrisville, N.C., USA).

1.2 Western Blot Analysis
H2122, H358 and A549 NSCLC cells were rinsed with phosphate-buffered saline (PBS) and lysed in radioimmunoprecipitation assay (RIPA) lysis buffer (Beyotime, China) supplemented with a protease and phosphatase inhibitor cocktail (Thermo Scientific 78440, USA) once for 30 minutes. Cell lysates were centrifuged at 12,000 g for 10 minutes at 4° C. The supernatant was collected, and the protein concentration was calculated with a Bio-Rad detergent compatible (DC™) protein assay kit (Bio-Rad, Philadelphia, Pa., USA). 30 μg protein lysates were loaded and separated by 10% sodium dodecyl sulfate (SDS)-polyacrylamide gel electrophoresis and transferred to a nitrocellulose (NC) membrane. The membranes were incubated with the primary antibody (1:2000) and then with a fluorescence-conjugated secondary antibody (1:10000). Glyceraldehyde 3-phosphate dehydrogenase (GAPDH) was used as the loading control for normalization. The signal of the membranes was scanned with a LI-COR Odyssey Scanner (Belfast, Me., USA).

1.3 RAS Binding Domain Pull Down
KRAS activation was determined using the rat sarcoma (RAS) activation assay kit (Millipore, 17-218) in accordance with the manufacturer's guidelines. Cell lysates were prepared using $Mg2^+$ Lysis/wash buffer (MLB). Samples were incubated with 10 μg RAS assay reagent and incubated for 45 minutes at 4° C. Agarose beads were pelleted by centrifugation and washed 3 times with MLB. Agarose beads were re-suspended in loading buffer. Samples were subjected to western blotting, as previously described, and the blots were probed using anti-K-Ras antibody (sc-30, Santa Cruz Biotechnology (SANTA)).

1.4 Apoptosis Analysis
H2122, A549 and H358 NSCLC cells were plated in a 6-well plate with $2.0×10^5$ cells/well and cultured overnight for attachment. After treatment with compound K017-0105 at 0, 5, 10, 20, 40 μM for 24 h, all cells were harvested by trypsinization and centrifuged at room temperature at 1000 rotations per minute (RPM) for 5 minutes. Cells were re-suspended in 100 μL 1× binding buffer and stained with Annexin V and propidium iodide (PI) staining solution for 15 minutes at room temperature in the dark. Apoptotic cells were quantitatively counted by a BD FACSAria III Flow Cytometer.

1.5 Statistical Analysis
All analytical data are presented as mean±standard error of the mean (SEM). The statistical significant differences were analyzed by one-way analysis of variance (ANOVA) for comparison tests, using GraphPad Prism Version 6.0 software (San Diego, Calif., USA).

Example 2: The Cytotoxic Effect of Compound K017-0105 on H2122, H358 and A549 NSCLC Cells FIG. 1 shows four graphs 100 illustrating the cytotoxic effect of the compound K017-0105 on H2122, H358 and A549 NSCLC cells and normal CCD-19Lu cells for 72 h.

Figure 1:
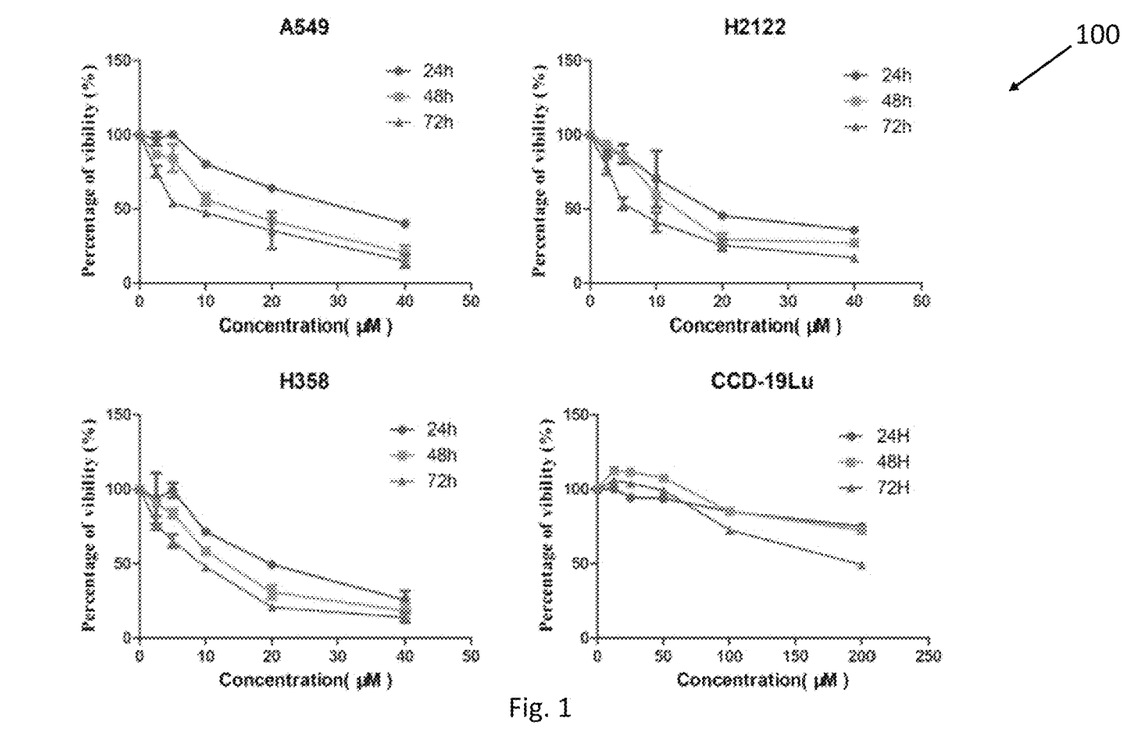
FIG. 1 illustrates the results of an 3-(4,5-Dimethylthiazol-2-yl)-2,5-Diphenyltetrazolium Bromide (MTT) colorimetric assay showing the cytotoxic effect of compound of formula I (i.e. compound K017-0105) on A549, H2122 and H358 non-small cell lung cancer (NSCLC) cells in accordance with an example embodiment.

As shown in FIG. 1, the 3-(4,5-Dimethylthiazol-2-yl)-2, 5-Diphenyltetrazolium Bromide (MTT) assay showed that compound K017-0105 exhibited significant cytotoxicity on H2122, H358 and A549 NSCLC cells. Compound K017-0105 inhibited cell proliferation of H2122, H358 and A549 NSCLC cell lines.

Figure 2:
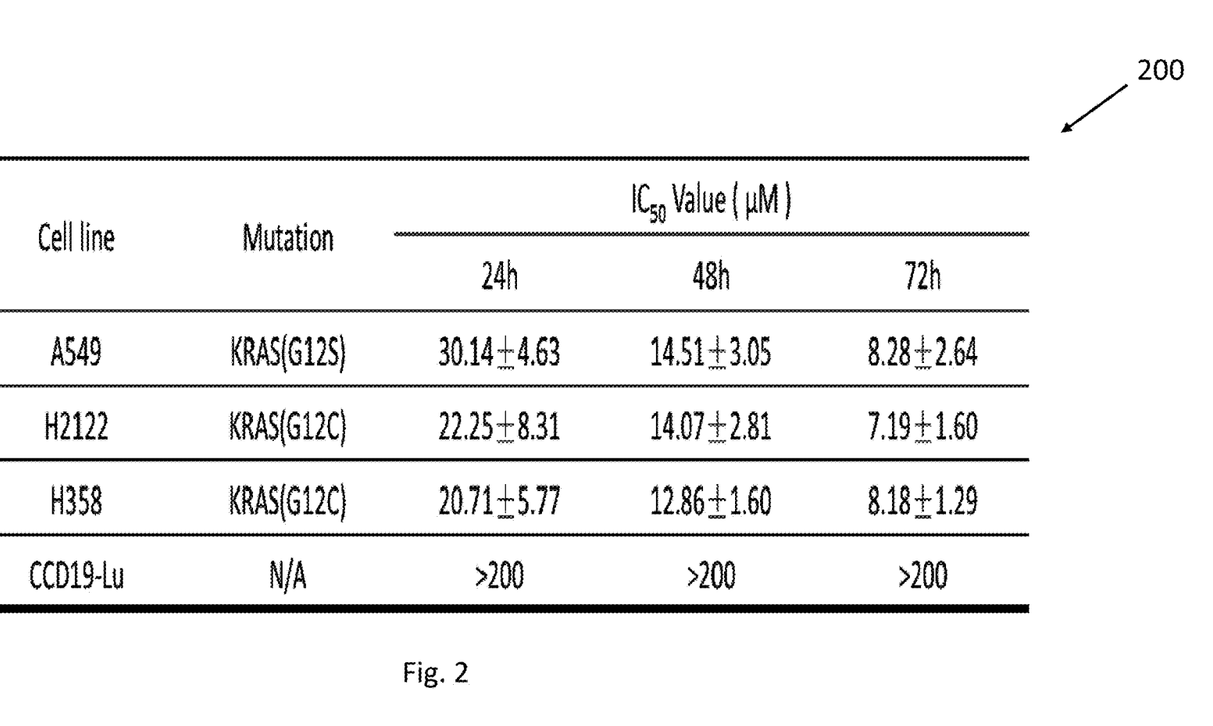
FIG. 2 illustrates the $IC_{50}$ values of K017-0105 on H2122, H358, A549 NSCLC cells and CCD-19Lu cells.

FIG. 2 shows a table 200 illustrating that the IC$_{50}$ values of compound K017-0105 on H2122, H358 and A549 NSCLC cells are 7.19±1.60 μM, 8.18±1.29 μM and 8.28±2.64 μM, respectively, after 72 h treatment. FIG. 2 also illustrates the effect of compound K017-0105 on normal CCD-19Lu lung cells at 72 h.

As shown in FIGS. 1 and 2, compound K017-0105 exhibits no cytotoxicity on CCD-19Lu cells. The IC$_{50}$ value of the normal lung cell is more than 5 fold in comparison with the other three NSCLC cell lines.

Figure 3:
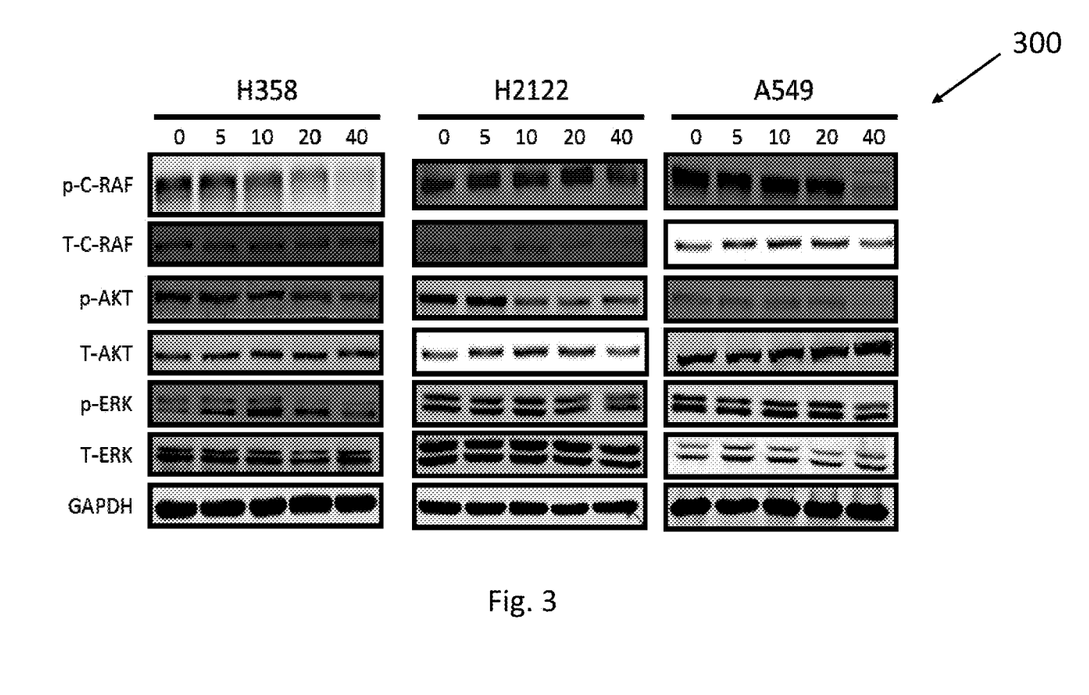
FIG. 3 illustrates that compound K017-0105 inhibits the levels of phospho-proto-oncogene c-RAF (p-CRAF), p-Akt and phospho-extracellular signal-regulated kinases (p-ERK) in A549, H2122 and H358 NSCLC cells in accordance with an example embodiment.

Example 3: Compound K017-0105 Decreases Activity of Rat Sarcoma (RAS) Downstream Signaling FIG. 3 shows a western blot analysis 300 illustrating the inhibitory effect of compound K017-0105 on KRAS downstream signaling pathways in H358, H2122 and A549 NSCLC cell lines. Untreated cells were used as a control. A representative of at least three independent experiments for each cell line is shown.

As shown in FIG. 3, compound K017-0105 decreased the levels of phospho-proto-oncogene c-RAF (p-CRAF), p-Akt and phospho-extracellular signal-regulated kinases (p-ERK) in H2122, A549 and H358 NSCLC cells when compared with untreated control cells.

Figure 4:
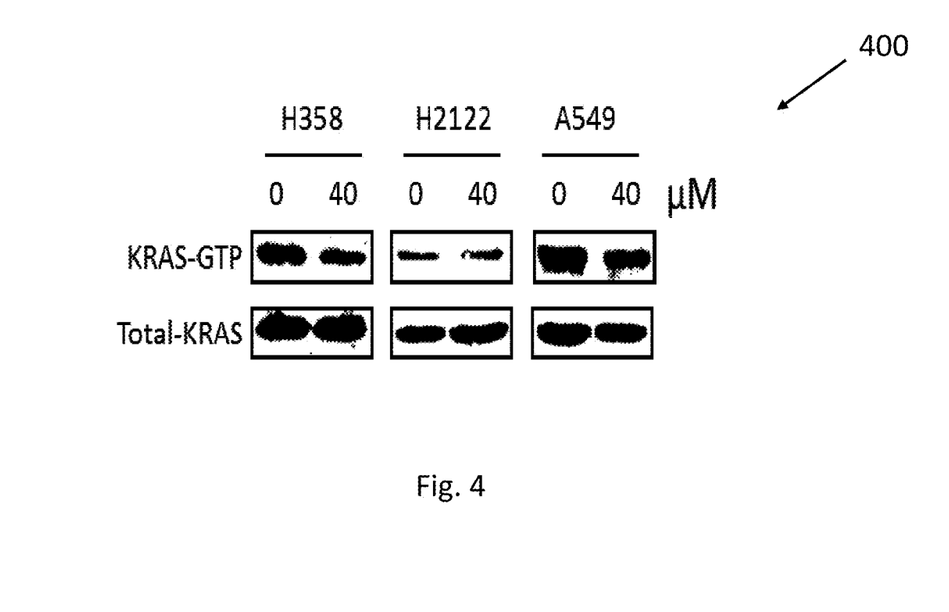
FIG. 4 illustrates the inhibitory effect of compound K017-0105 on the level of active V-Ki-ras2 Kirsten rat sarcoma viral oncogene homolog (KRAS) in H358, H2122 and A549 NSCLC cells as determined by a rat sarcoma (RAS)-binding domain pull-down (RBD-PD) assay in accordance with an example embodiment.

Example 4: Compound K017-0105 Inhibits the Level of Guanosine Triphosphate (GTP)-Bound KRAS at 400

FIG. 4 shows the results of the RAS-binding domain pull down assay 400 illustrating that 400 of compound K017-0105 inhibited the level of GTP-bound KRAS in H358, H2122 and A549 NSCLC cells following 24 hour treatment.

Example 5: Compound K017-0105 Induced Apoptosis and LED to Cell Cycle Arrest in H358, H2122 and A549 NSCLC Cells The ability of compound K017-0105 in inducing apoptosis in H2122, H358 and A549 NSCLC cells was examined. H2122, H358 and A549 NSCLC cells were treated with compound K017-0105 at different concentrations (0, 5, 10, 20 and 40 μM) for 24 h. These cells were stained with Annexin V-FITC/PI, and cell cycle arrest was detected by flow cytometry.

Figure 5A:
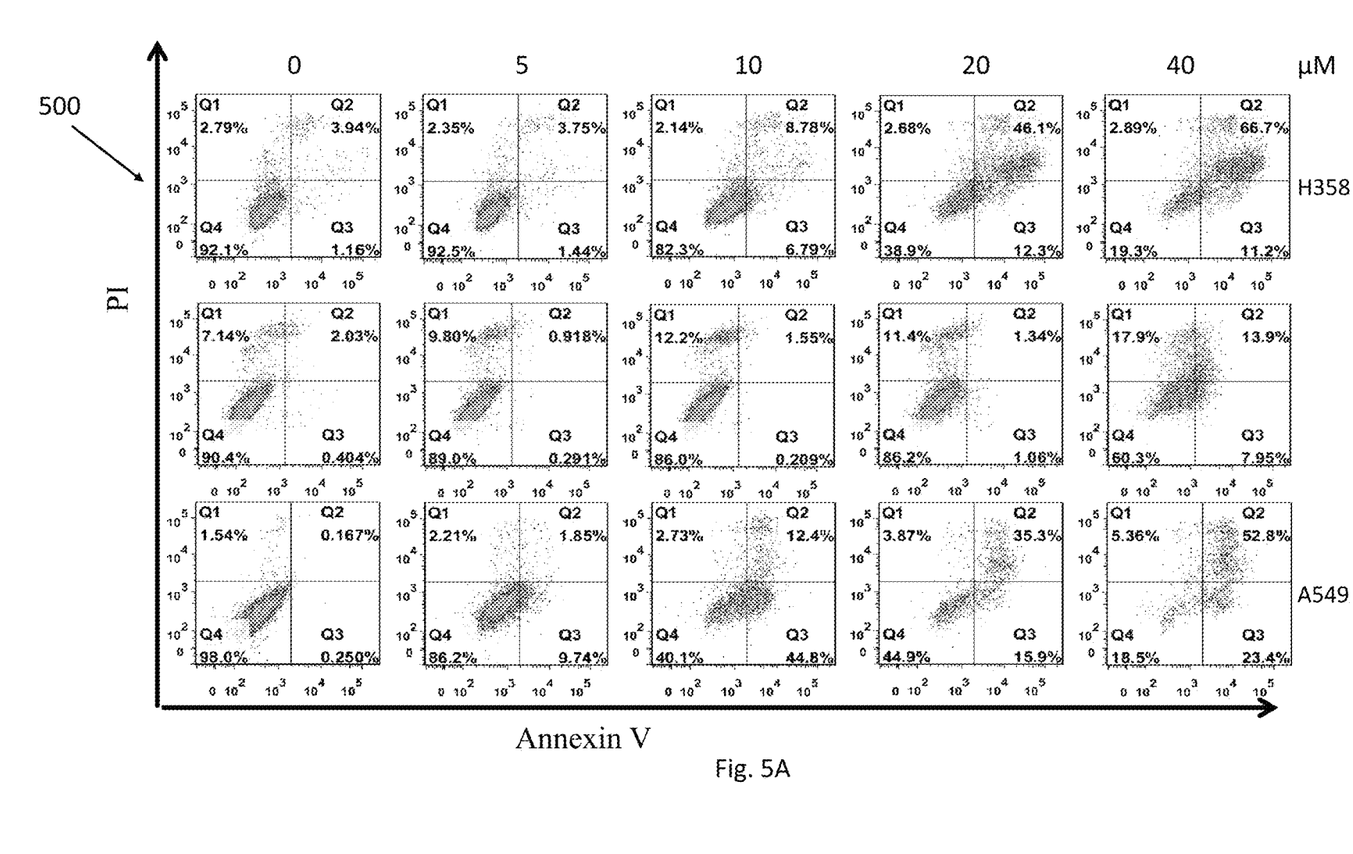
FIG. 5A shows a flow cytometric analysis on the cell cycle arrest of H2122, H358 and A549 NSCLC cells after treatment with compound K017-0105 for 24 hours in accordance with an example embodiment.

FIG. 5A shows flow cytometric analysis 500 of the apoptosis level after treatment of H358, H2122 and A549 cells with compound K017-0105 for 24 h.

Figure 5B:
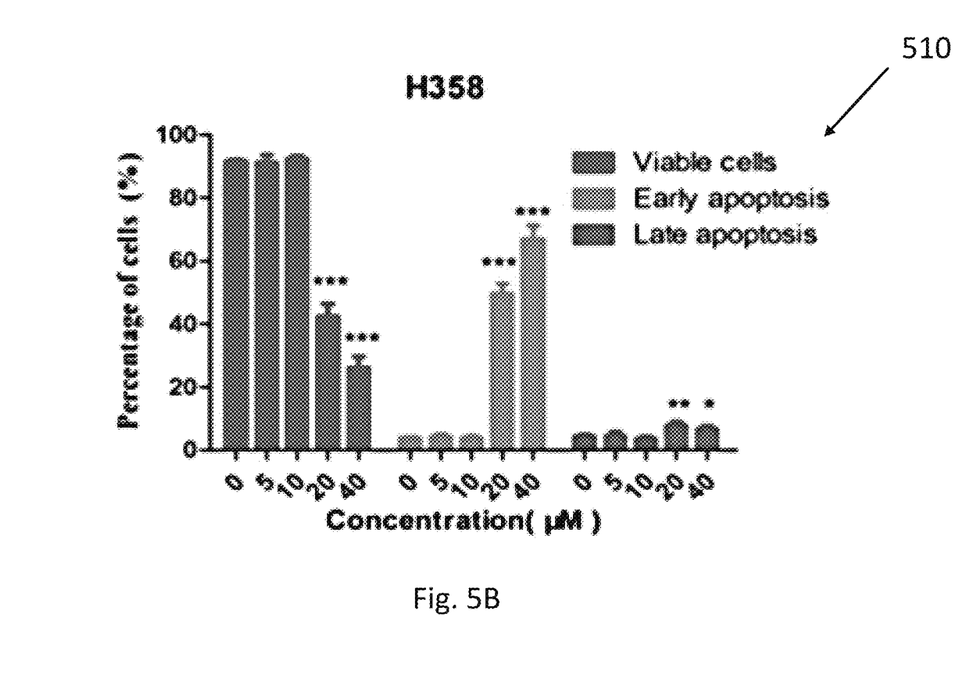
FIG. 5B show statistical analysis of apoptosis data of FIG. 5A for H358 cells in accordance with an example embodiment.
Figure 5C:
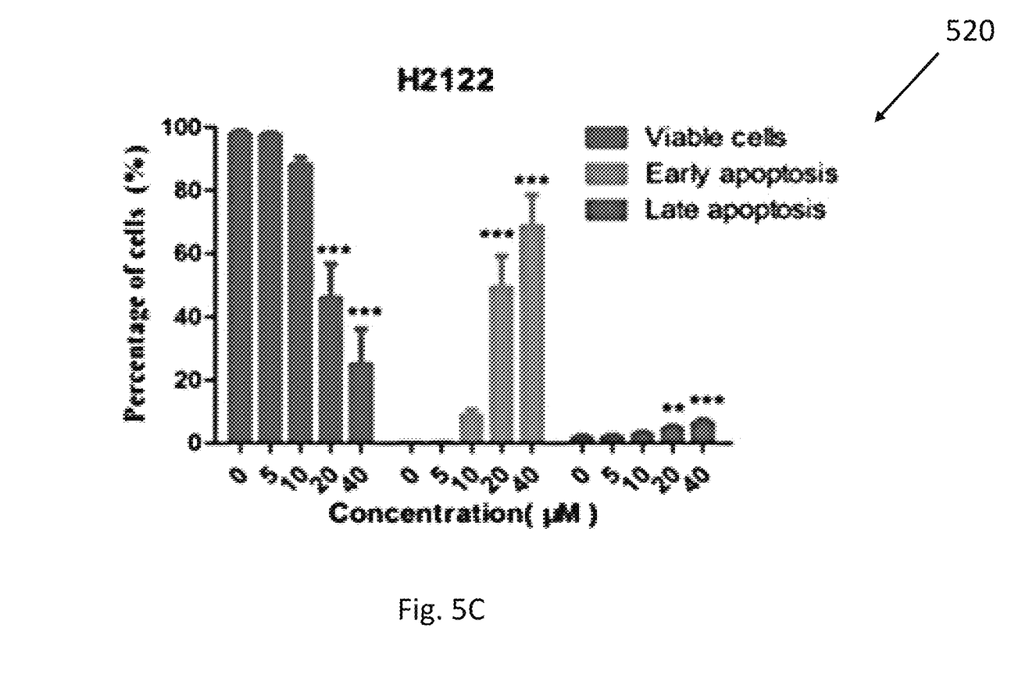
FIG. 5C show statistical analysis of apoptosis data of FIG. 5A for H2122 cells in accordance with an example embodiment.
Figure 5D:
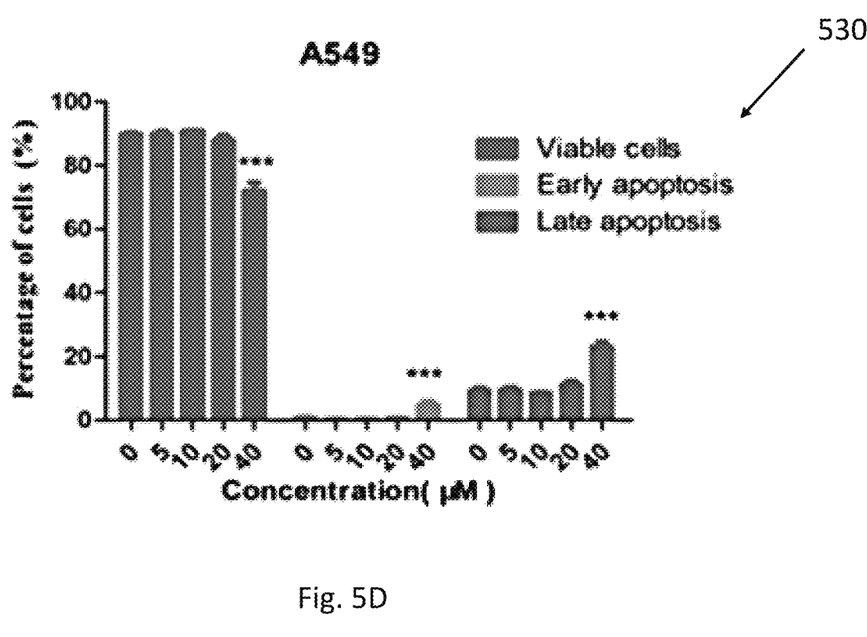
FIG. 5D show statistical analysis of apoptosis data of FIG. 5A for A549 cells in accordance with an example embodiment.

FIGS. 5B, 5C and 5D show cell cycle distribution 510, 520, 530 for 24 h. All data is presented as mean±SEM (n=3, *p<0.05, p<0.01, *p<0.001).

Figure 5E:
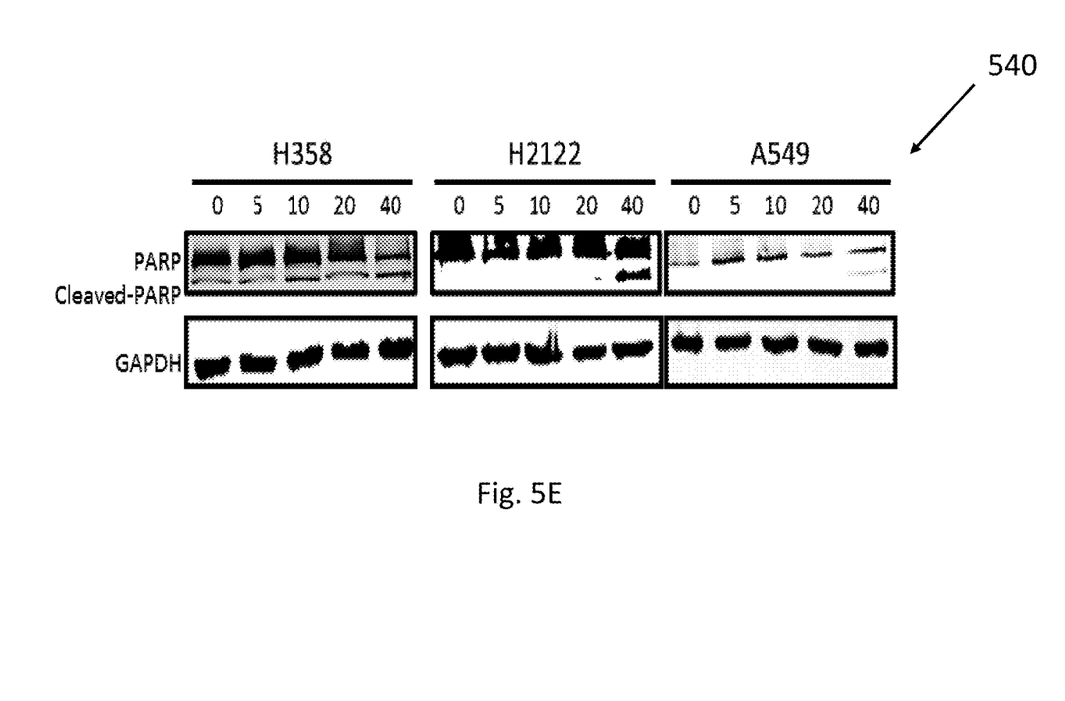
FIG. 5E shows the detection of apoptosis marker poly (ADP-ribose) polymerase (PARP) in H358, H2122 and A549 NSCLC cells following 24 hour treatment with compound K017-0105 in accordance with an example embodiment.

FIG. 5E shows a western blot analysis 540 illustrating that poly ADP ribose polymerase (PARP), a marker of apoptosis, was detected 24 h after treatment of H358, H2122 and A549 NSCLC cells with compound K017-0105. GAPDH was used as a loading control. The results show that compound K017-0105 significantly induced apoptosis in H2122, H358 and A549 NSCLC cell lines.

Therefore, compound K017-0105 of formula I inhibits the progress of tumor growth such that the compound can be used to treat cancer cells with a KRAS mutation. The mutation can be an amino acid substitution from a glycine to a cysteine at codon 12 of KRAS (KRAS$^{G12C}$ mutation) or an amino acid substitution from a glycine to a serine at codon 12 of KRAS (KRAS$^{G12S}$ mutation). Compound K017-0105 can be used to treat lung cancer, NSCLC or lung adenocarcinoma by inhibiting the level of GTP-bound KRAS and/or decreasing the phosphorylation of CRAF, ERK and Akt.

Figure 6:
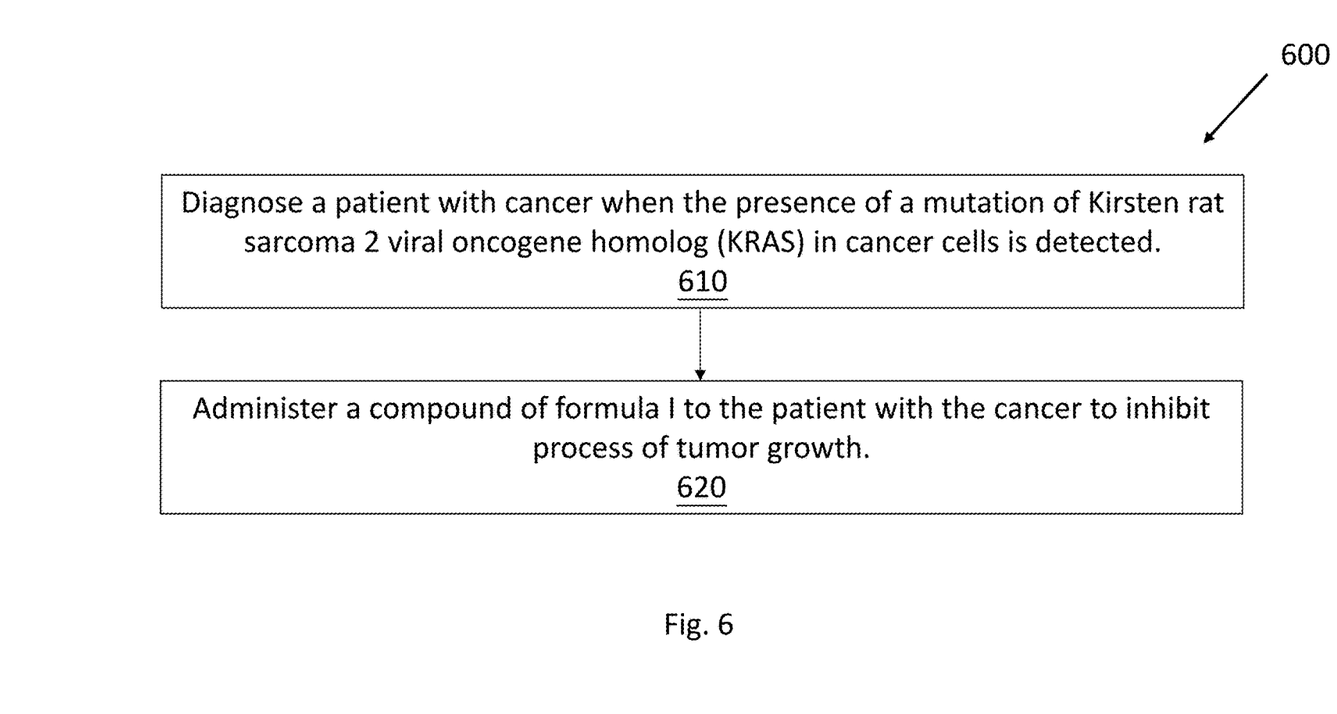
FIG. 6 shows a method to inhibit progress of tumor growth in a patient with cancer in accordance with an example embodiment.

FIG. 6 is a flow chart 600 illustrating a method to inhibit progress of tumor growth in a patient with cancer in accordance with an example embodiment.

Block 610 states diagnose a patient with cancer when the presence of a mutation of KRAS in cancer cells is detected.

In an example embodiment, a mutation analysis of cancer cells is conducted to detect the presence of a KRAS mutation. In an example embodiment, the mutation analysis can be conducted using methods that include, but are not limited to, one or more of the following: polymerase chain reaction (PCR) to amplify the appropriate region of the KRAS gene and distinguish wild type from mutant sequences, nucleic acid sequencing, allele-specific PCR methods, single-strand conformational polymorphism analysis, melt-curve analysis, probe hybridization, etc.

In a further example embodiment, a mutation analysis of codon 12 in KRAS is conducted. If the cancer patient has a mutant KRAS at codon 12 resulting from amino acid substitution of glycine (G) to cysteine (C), the patient will be diagnosed as having cancer cells with a KRAS$^{G12C}$ mutation. If the cancer patient has a mutant KRAS at codon 12 resulting from amino acid substitution of glycine (G) to serine (S), the patient will be diagnosed as having cancer cells with a KRAS$^{G12S}$ mutation.

Block 620 states administer the compound of formula I to the patient with the cancer to inhibit progress of tumor growth.

In an example embodiment, the compound is administered directly or in the form of pharmaceutical compositions with suitable carriers or excipients. In one example embodiment, suitable routes of administration may, for example, include oral, rectal, transmucosal, nasal, or intestinal administration and parenteral delivery. The compound or the pharmaceutical composition that includes the compound can be administered locally. For example, the compound can be delivered via injection or in a targeted drug delivery system, such as a depot or sustained release formulation.

Figure 7:
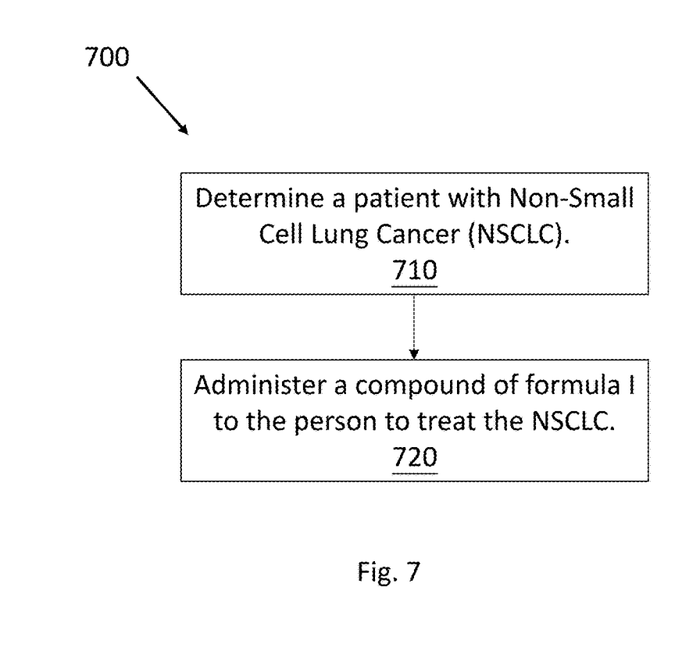
FIG. 7 shows a method to treat NSCLC in a patient in accordance with an example embodiment.

FIG. 7 is a flowchart 700 illustrating a method to treat NSCLC in a patient in accordance with an example embodiment.

Block 710 states determine a patient with NSCLC. In one example embodiment, it can be determined whether the patient suffers from NSCLC using methods such as chest X-ray, multi-detector computerized tomography scan, magnetic resonance imaging, positron emission tomography, fine and core needle biopsies of the lung, bronchoscopy, endobronchial ultrasound, navigational bronchoscopy, etc.

Block 720 states administer the compound of formula I to the patient to treat the NSCLC. In one example embodiment, the compound is administered directly or in pharmaceutical compositions with suitable carriers or excipients. In one example embodiment, suitable routes of administration may, for example, include oral, rectal, transmucosal, nasal, or intestinal administration and parenteral delivery. The compound or the pharmaceutical composition that includes the compound can be administered locally. For example, the compound can be delivered via injection or in a targeted drug delivery system, such as a depot or sustained release formulation. In one example embodiment, the compound is administered in conjunction with administration of other chemo-drugs that treat NSCLC, such as Tarceva, etc.

Figure 8:
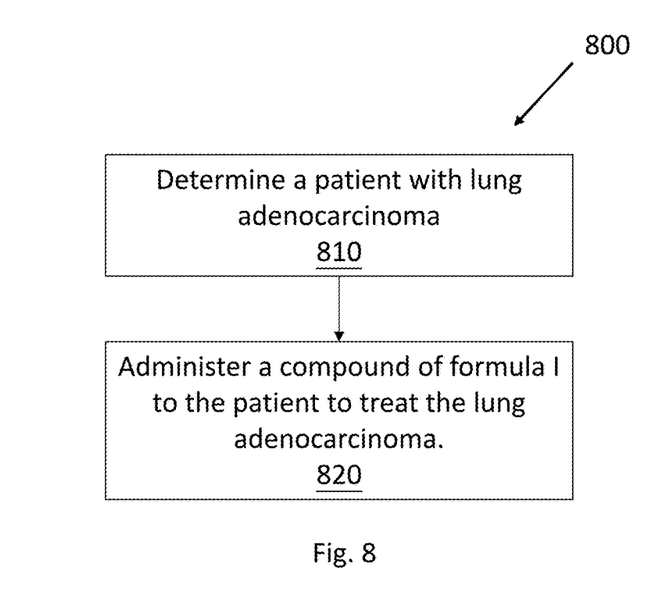
FIG. 8 shows a method to treat lung adenocarcinoma in a patient in accordance with an example embodiment.

FIG. 8 is a flowchart 800 illustrating a method to treat lung adenocarcinoma in a patient in need of such treatment in accordance with an example embodiment.

Block 810 states determine a patient with lung adenocarcinoma. In one example embodiment, methods such as chest computerized tomography scan, sputum cytology, bronchoscopy, positron emission tomography scan, etc., can be used to determine whether a patient has lung adenocarcinoma.

Block 820 states administer the compound of formula I to the patient to treat the lung adenocarcinoma. In one example embodiment, the compound is administered directly or in pharmaceutical compositions along with suitable carriers or excipients. In one example embodiment, suitable routes of administration may, for example, include oral, rectal, transmucosal, nasal, or intestinal administration and parenteral delivery. The compound or the pharmaceutical composition that includes the compound can be administered locally. For example, the compound can be delivered via injection or in a targeted drug delivery system, such as a depot or sustained release formulation.

As used herein, the term "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "therapeutically effective amount" refers to any amount of a compound which, as compared to a corresponding patient who has not received such amount, results in improved treatment, healing, prevention, or amelioration of a disease, disorder, or side effect, or a decrease in the rate of advancement of a disease or disorder.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "administration" or "administering" of the patient compound refers to providing a compound of an example embodiment and/or prodrugs thereof to a patient in need of treatment.

What is claimed is:

1. A method of treating non-small cell lung cancer (NSCLC) in a patient, comprising:
    administering a therapeutically effective amount of a compound to the patient to treat the NSCLC,
    wherein the compound is represented by formula I formula I 2. The method of claim 1, wherein cells of the NSCLC express a mutant V-Ki-ras2 Kirsten rat sarcoma viral oncogene homolog (KRAS).

3. The method of claim 2, wherein the mutant KRAS includes an amino acid substitution from a glycine to a cysteine at codon 12.

4. The method of claim 2, wherein the mutant KRAS includes amino acid substitution from a glycine to a serine at codon 12.

5. The method of claim 2, wherein the mutant KRAS causes an increased level of guanosine triphosphate (GTP)-bound KRAS, and the compound inhibits the level of GTP-bound KRAS to treat the NSCLC.

6. The method of claim 2, wherein the mutant KRAS activates phosphorylation of proto-oncogene c-RAF (CRAF), extracellular signal-regulated kinases (ERK) and Akt, and the compound inhibits the phosphorylation of CRAF, ERK and Akt to treat the NSCLC.

7. A method of treating lung adenocarcinoma in a patient, comprising:
    administering a therapeutically effective amount of a compound to the patient to treat the lung adenocarcinoma,
    wherein the compound is represented by the formula I formula I 8. The method of claim 7, wherein tumor cells of the lung adenocarcinoma have a mutant V-Ki-ras2 Kirsten rat sarcoma viral oncogene homolog (KRAS).

9. The method of claim 8, wherein the mutant KRAS includes an amino acid substitution from a glycine to a cysteine at codon 12.

10. The method of claim 8, wherein the mutant KRAS includes amino acid substitution from a glycine to a serine at codon 12.

11. The method of claim 8, wherein the compound inhibits an increased level of guanosine triphosphate (GTP)-bound KRAS that is caused by the mutant KRAS so that the lung adenocarcinoma is treated.

12. The method of claim 8, wherein the mutant KRAS activates phosphorylation of proto-oncogene c-RAF (CRAF), extracellular signal-regulated kinases (ERK) and Akt, and the compound inhibits the phosphorylation of CRAF, ERK and Akt to treat the lung adenocarcinoma.

13. The method of claim 7, wherein the patient has non-small cell lung cancer (NSCLC).

14. A method of inhibiting progress of tumor growth in a patient with cancer, comprising:
    diagnosing the patient with the cancer when the presence of a mutation of V-Ki-ras2 Kirsten rat sarcoma viral oncogene homolog (KRAS) in cancer cells is detected; and
    administering a compound to the patient with the cancer to inhibit the progress of tumor growth, wherein the compound is represented by formula I formula I 15. The method of claim 14, wherein the mutation of KRAS includes an amino acid substitution from a glycine to a cysteine at codon 12.

16. The method of claim 14, wherein the mutation of KRAS includes amino acid substitution from a glycine to a serine at codon 12.

17. The method of claim 14, wherein the compound inhibits an increased level of guanosine triphosphate (GTP)-bound KRAS that is caused by the mutation of KRAS so that the cancer is treated.

18. The method of claim 14, where the mutation of KRAS activates phosphorylation of proto-oncogene c-RAF (CRAF), extracellular signal-regulated kinases (ERK) and Akt, and the compound inhibits the phosphorylation of CRAF, ERK and Akt to treat the cancer.

19. The method of claim 14, wherein the patient has non-small cell lung cancer (NSCLC).

20. The method of claim 14, wherein the patient has lung adenocarcinoma.

* * * * *